United States Patent [19]

Chang et al.

[11] 4,066,460
[45] Jan. 3, 1978

[54] IMAGING AND RECORDING OF INFORMATION UTILIZING TELLURIUM TETRAHALIDE

[75] Inventors: Yew C. Chang, Oakville, Canada; Stanford R. Ovshinsky, Bloomfield Hills; Ronald W. Citkowski, Pleasant Ridge, both of Mich.

[73] Assignee: Energy Conversion Devices, Inc., Troy, Mich.

[21] Appl. No.: 596,616

[22] Filed: July 17, 1975

Related U.S. Application Data

[63] Continuation-in-part of Ser. No. 400,849, Sept. 26, 1973, abandoned.

[30] Foreign Application Priority Data

July 17, 1974 United Kingdom ............... 31676/74

[51] Int. Cl.$^2$ .......................... G03C 5/24; G03C 1/00
[52] U.S. Cl. ............... 96/48 R; 96/48 HD; 96/48 QP; 96/88
[58] Field of Search ............ 96/48 HD, 88, 1.5, 48 R, 96/48 QP

[56] References Cited

U.S. PATENT DOCUMENTS

| | | | |
|---|---|---|---|
| 3,147,117 | 9/1964 | Wainer et al. | 96/48 R |
| 3,527,639 | 9/1970 | Moraw | 96/90 R |
| 3,579,342 | 5/1971 | Strilko | 96/90 R |
| 3,700,448 | 10/1972 | Hillson et al. | 96/88 |
| 3,819,377 | 6/1974 | Klose et al. | 96/48 HD |

OTHER PUBLICATIONS

Boudreaux, et al. J. Amer. Chem. Soc., vol. 85, No. 14, July 20, 1963, pp. 2039–2043.
Boudreaux, et al. J. Amer. Chem. Soc., vol. 80 (1957), pp. 1588–1590.

*Primary Examiner*—Won H. Louie, Jr.
*Attorney, Agent, or Firm*—Wallenstein, Spangenberg, Hattis & Strampel

[57] ABSTRACT

Selected areas of a layer comprising a tellurium tetrahalide imaging material, exemplified by tellurium tetrachloride, are subjected to the imaging effect of imaging energy, and of developing energy causing a chemical change in the tellurium tetrahalide imaging material in the imaged areas accompanied by a change in the detectable characteristic of the imaged areas. The aforesaid imaging material is extended in a matrix of a film-forming material together with a sensitizer. The application of the energy is advantageously effected in two steps, an imaging step employing imaging energy and producing a latent image, followed by a development step employing developing energy and producing the detectable recorded information or image.

30 Claims, 5 Drawing Figures

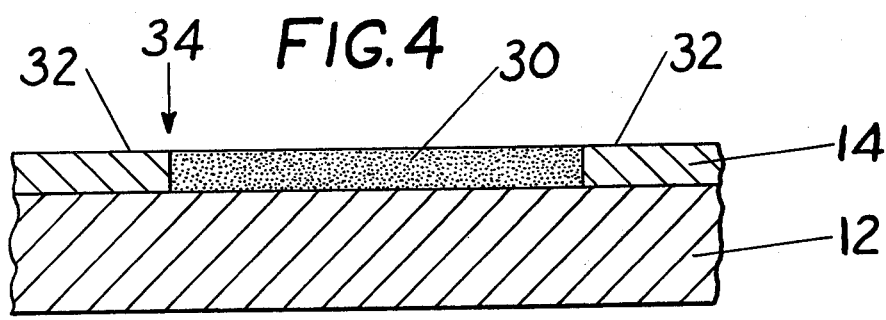
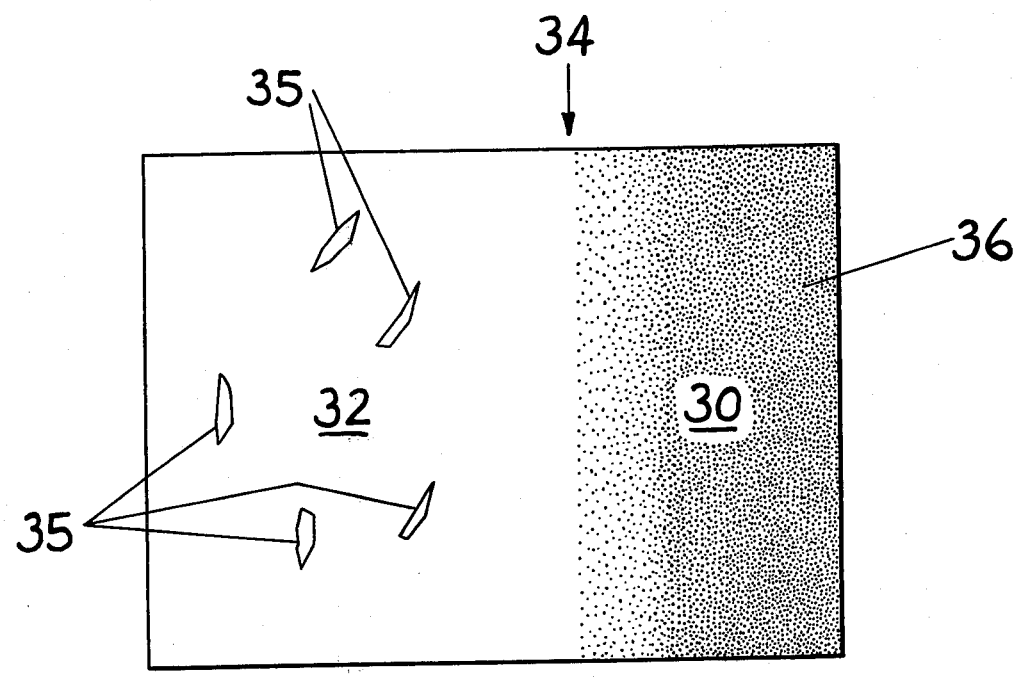

IMAGING AND RECORDING OF INFORMATION UTILIZING TELLURIUM TETRAHALIDE

CROSS-REFERENCE TO RELATED APPLICATION

This application is a continuation-in-part of application Ser. No. 400,849, filed Sept. 26, 1973, now abandoned.

This invention relates to improvements in recording information and producing images.

Various methods are known for producing images or duplicates of images. The imaging materials used are, in certain cases, particular inorganic compounds and, in other cases, particular organic compounds. Some of these heretofore known methods employ mixtures of inorganic compounds such as silver halide with one or more particular types of organic compounds as sensitizers. More specifically, it has heretofore been known, as shown in German Pat. No. 2,022,260, to produce images by coating or depositing on a substrate, such as paper, glass, or synthetic polymers, inorganic compound light sensitive substances such as cupric oxide, bismuth subchloride, mercury chloride and tellurium dihalides such as tellurium dichloride, tellurium dibromide, tellurium chlorobromide and tellurium iodidibromide. The tellurium dihalides are shown to be made by initially preparing the tetrahalide, e.g. $TeCl_4$, $TeBr_4$ or $TeI_4$, and then melting together said tetrahalide with metallic tellurium powder and grinding to a powder which is generally yellow-gray or black. The resulting tellurium dihalides are applied to an adhesive strip which is then moistened with acetone, ethanol, isopropanol or other organic liquids and exposed to a source of energy such as a Xenon luminous arc to produce a visible image. The patent teaches the development of images produced in accordance with the invention thereof by liquid developers such as water solutions of sodium hydroxide or other alkali metal hydroxides, or water solutions of mineral acids or of organic acids such as sulfuric acid, nitric acid, phosphoric acid, acetic acid, citric acid, formic acid, as well as with other liquid developers such as ethyl alcohol, ethyl ether, chloroform, etc. Such procedures are, generally speaking, cumbersone, in certain cases hazardous, time consuming and quite unsatisfactory. Tellurium dichloride, for instance, is black in color, whereas tellurium tetrachloride is white in color. Hence, the latter, when exposed to imaging energy, turns dark in areas subject to said energy, leaving a white background in the unexposed areas, a situation which does not obtain in the case of the use of tellurium dichloride.

The present invention is concerned with a new imaging system which employs certain tellurium tetrahalides, namely, those in which the halide is at least one member selected from the group consisting of chlorine and bromine, especially chlorine. Certain of these imaging materials can be represented by the formula $TeCl_nBr_m$ where n is an integer from 2 to 4 and m is an integer from 0 to 2 with the proviso that the sum of n and m equals 4. In the particularly important embodiments of the invention, the aforesaid imaging material is incorporated into a matrix together with a sensitizer, all as hereafter described in detail. The resulting combination of materials is formed into a thin film or layer which is capable of producing a latent image when subjected to imaging energy as, for instance, electromagnetic radiation. The resulting latent image may then readily be developed into an image of excellent contrast by subjection to a source of developing energy, generally in the form of heat energy.

Accordingly, the invention provides a novel method and novel compositions for producing records of retrievable information, for instance images and duplicates of existing images, which are predicated on a layer which comprises certain tellurium tetrahalides as imaging materials, which have one detectable characteristic and which are capable of undergoing a chemical change in response to the application of imaging energy to produce a material of different chemical character or composition, having another detectable characteristic. In accordance with the method, imaging energy is applied to at least a certain portion of the layer comprising the material to bring about the chemical change in the imaging material, in the portion of the layer subjected to the energy, which chemically changed imaging material has at least one detectable characteristic which differs from the characteristics of the starting imaging material, and which difference in detectable characteristics may be detected visually or by any suitable detection means or read out means. The material having a different chemical character or composition and different detectable characteristics, resulting from the imaging step, will sometimes hereinafter be called the image former.

As noted above, the imaging materials utilized in the practice of the present invention comprise tellurium tetrahalides such as $TeCl_4$, $TeBr_4$, $TeCl_2Br_2$, $TeCl_3Br$ and $TeClBr_3$, $TeCl_4$ being especially useful in the practice of the present invention. They should be soluble or homogeneously dispersible in the matrix mateial described hereafter.

When tellurium tetrachloride is dissolved in an organic solvent, for instance, tetrahydrofuran (THF) and then coated onto a substrate and the organic solvent only partially evaporated off whereby to leave the surface wet or moist, and then exposed to imaging energy, such as ultraviolet light, through a mask, the image is formed, and development by heat or like energy is unnecessary and serves no enhancement effect. This may conveniently here be referred to as constituting a wet process. No sensitizer is necessary where, for instance, ultraviolet light constitutes the imaging energy. Other tellurium tetrahalides are distinctly less satisfactory than tellurium tetrachloride when this wet process is employed.

It is, however, especially advantageous to utilize the tellurium tetrachloride or other tellurium tetrahalide in the form of a dry film, by incorporating it into a matrix in conjunction with a sensitizer, and laying the same down in the form of a dry-to-the-touch thin film, particularly on a substrate. In this form, it is then subjected to imaging energy through a mask to produce an image or a latent image which is then developed by heat or a development source of energy to produce the final image. The imaging energy, depending upon the sensitizer utilized, may be ultraviolet light or visible light or other energy sources as pointed out hereafter.

The matrix materials, into which the imaging materials, and the separate sensitizers when employed, are incorporated to produce the imaging film or coating, are solids at room temperature, and they can be selected from a relatively large number of materials. They should desirably be at least in part of amorphous character and it is especially desirable that they be glassy, polar amorphous materials having a glass transition temperature, which desirably should not exceed about 200° C and may be as low as about 50° C, and, better still, should be within the range of about 80°-120° C. They are generally polymeric materials. Illustrative thereof are cyanoethylated starches, celluloses and amyloses having a degree of substitution of cyanoethlation of $\geq 2$; polyvinyl-benzophenone; polyvinylidene chloride; polyethylene terephthalate ("MYLAR"); cellulose esters and ethers such as cellulose acetate, cellulose propionate, cellulose butyrate, methyl cellulose, ethyl cellulose, hydroxypropyl cellulose; polyvinylcarbazole; polyvinyl chloride; polyvinyl methyl ketone; polyvinyl alcohol; polyvinylpyrrolidone; polyvinyl methyl ether; polyacrylic and polymethacrylic alkyl esters such as polymethyl methacrylate and polyethyl methacrylate; copolymer of polyvinyl methyl ether and maleic anhydride; various grades of polyvinyl formal resins such as so-called 12/85, 6/95 E, 15/95 S, 15/95 E, B-79, B-98, and the like, sold under the trademark "FORMVAR" —(Monsanto Company). Of especial utility is polyvinyl formal 15/95 E which is a white, free flowing powder having a molecular weight in the range of 24,000 – 40,000 and a formal content expressed as % polyvinyl formal of approximately 82%, possessing high thermal stability, excellent mechanical durability, and resistance to such materials as aliphatic hydrocarbons, and mineral, animal and vegetable oils. These polymeric materials or resins and their preparation are well known to the art. In addition to their functioning as carriers for and holding together in a unitary composition the imaging materials, sensitizers and any other ingredients which may be incorporated into the imaging film or coating or layer and their functioning as dry or essentially dry film-forming materials to provide thin films and providing mechanical durability in the finished imaged film, at least many of them appear also to play a chemical or physical role in the imaging process by providing, importantly, a source of readily easily abstractable hydrogen and, thus, appear to play a significant role in the latent image formation mechanism, as discussed hereafter. In certain instances, it may be desirable to decrease the viscosity of the matrix, which can be done, by way of illustration, by the addition of certain plasticizers, for instance, dibutylphthalate or diphenylphthalate, which additions tend to result in the production of images desirably of higher optical densities but which, however, also tend to have the disadvantage of increasing background fogging.

It may be noted that matrix materials of the type which contain basic groups may complex with the imaging materials and, therefore, to the extent that such complexing may occur, the use of such matrix materials should be avoided.

The sensitizers which are useful in the practice of the present invention, in the production of dry-to-the-touch films, can be selected from a large group. They should be soluble or homogeneously dispersible in the matrix material. Their selection for use in any particular imaging compositions is influenced, in part, by the spectral sensitivity ranges desired. Thus, for instance, in the case of ultraviolet (UV) and visible sensitizers, the following are illustrative of those which can be employed and their approximate spectral sensitivity range (nm):

| Sensitizer | Spectral Sensitivity Range (nm) |
|---|---|
| 9, 10-phenanthrenequinone | 200 – 400 – 500 |
| | U.V. Visible |
| 1,1'-dibenzoylferrocene | 400 – 600 |
| 1-phenyl-1,2-propanedione | 400 – 500 |
| 2-hydroxyl-1,4-naphthoquinone | 400 – 500 |
| Benzil | 400 – 450 |
| Furil | 400 – 480 |
| Diacetylferrocene | 400 – 450 |
| Acetylferrocene | 400 – 450 |
| 1,4-bis(phenyl glyoxal)benzene | 400 – 500 |
| O-Naphthoquinone | Up to about 560 |
| 4,5-Pryinequinone | " " " 530 |
| 4,5,9,10-Pryinequinone | " " " 550 |

In the practice of the present invention, 9,10-phenanthrenequinone is especially satisfactory.

The following are illustrative sensitizers which are sensitive in the range of up to about 400 nm and, therefore, are useful only in the ultraviolet range: benzophenone; acetophenone; 1,5-diphenyl-1,3,5-pentanetrione; ninhydrin; 4,4'-dibromobenzophenone and 1,8-dichloroanthraquinone.

Various other sensitizers can be utilized, particularly those of the type of substituted or unsubstituted polynuclear quinones, of which class some have been mentioned above, and others of which are 1,2-benzanthraquinone; 2-methylanthraquinone; 1-chloroanthraquinone; 7,8,9,10-tetrahydronaphthacenequinone; 9,10-anthraquinone and 1,4-dimethylanthraquinone. It will be understood that not all sensitizers will be effective or equally effective, with each given imaging material, even taking into account the utilization of imaging energy in the nm sensitivity range of the sensitizer employed and that suitable selections of combinations of particular imaging materials and particular sensitizers will be required to be made for achieving desirable or optimum results. Such selections, however, can be made relatively readily.

In general, in connection with the foregoing matters, it may be noted that sensitizers have $n,\pi^*$ states, both singlet and triplet, of lower energies than $\pi,\pi^*$ states and, at least in most cases, compounds which have their $\pi,\pi^*$ states of lowest energy will not be photosensitively effective, although, in certain limited cases, compounds which fulfill the test of having lower energy $n \rightarrow \pi^*$ than $\pi \rightarrow \pi^*$ transitions do not function as photosensitive reactants. However, the above consideration is, in the main, an effective one for determining in advance whether a given compound will function as a photosensitizer for use in the practice of the present invention. In any event, a single preliminary empirical test in any given instance can readily be carried out if desired.

In the imaging compositions, the proportions of the matrix, the imaging material and the sensitizer are variable. In any event, generally speaking, excluding the organic solvent or solvents, where employed as described below, at least in most cases the matrix material, which is a normally solid material, that is, solid at room temperature, will be employed in amounts in excess of any one of the other materials and will also usually be present in major amount, that is, more than 50% and broadly in the range up to 90%, preferably about 60 to 70%, by weight, of the total materials present in the imaging composition. The imaging material, generally also a normally solid material, will usually or commonly be the next largest ingredient, and will ordinarily constitute from about 5 or 7 to about 30%, usually about 10 or 15 to 20%, by weight of the imaging composition. The sensitizer, which is usually a solid but may be a liquid at room temperature, will usually be employed in lesser proportions, commonly of the order of about 5 to 20%, usually about 6 to 15%, by weight, of the imaging composition, although, in certain cases the proportions thereof can be substantially higher, approximately or even exceeding somewhat the proportions of the imaging material. Again, and with further regard to the proportions of the aforesaid ingredients, it may be stated that the area density of the sensitizer, for instance, the 9,10-phenanthrenequinone, is desirably selected so that about 80% of the photons falling on the film in the region of the absorption bands of 9,10-phenanthrenequinone are absorbed. Considerably higher concentrations of 9,10-phenanthrenequionone would leave the dark side of the film unexposed and no advantage would thus be served. Again, in general and for optimal results in many cases, the mole concentration of the imaging material should be reasonably close to or roughly approximate that of the sensitizer. The concentration of the polymer matrix material should be sufficient to produce an essentially amorphous film without bringing about precipitation of the imaging material, the sensitizer and other supplemental ingredients when utilized. Excess polymer matrix material also tends to decrease the sensitivity of the film.

In certain cases, it may be desirable to include, in the imaging composition, additional or supplemental materials for obtaining certain or special effects. Thus, for example, it has been found that certain materials enhance the shelf life of unexposed virgin dry film compositions of the present invention and, in certain instances, also, they enhance the sensitivity of said film compositions. Illustrative embodiments of such additional or supplemental materials, which contain ether or polyether linkages in the molecules thereof, are such materials or polymers as polyethylene-20 sorbitan monolaurate; polyethylene-20 sorbitan monooleate; Polyox-10; Polyox-80; Polyox-750; polyethylene glycol-400-distearate; polyethylene glycol-600 distearate; poly (1,3-dioxolane), poly (tetrahydrofuran); poly (1,3-dioxane); polyacetaldehydes; polyoxymethylenes; fatty acid esters of polyoxymethylenes; poly (cyclohexane methylene oxide); poly (4-methyl-1,3-dioxane); polyoxetanes; polyphenylene oxides; poly [3,3-bis (halomethyl) oxycyclobutane]; poly (oxypropylene) glycol epoxy resins; and copolymers of propylene oxides and styrene oxides. Such materials can be incorporated in the imaging film compositions in varying amounts, generally from 5 to 20% by weight of the solid imaging film compositions. In certain cases they enhance or prolong the shelf life or storage life, under given storage conditions, as much as 50% or even very substantially more timewise, and, as indicated, they also, in various cases, effectively increase film sensitivity.

Again, the inclusion in the imaging films of reducing sugars has been found, generally speaking, to bring about an enhancement in density of the image area (O. D. image-O. D. background), when the film is imaged as disclosed above and then developed, for instance, at about 120°–150° C and for of the order of about 15 seconds, especially where the imaging film is freshly prepared or not older than about a day after initial preparation. Such films, when exposed to imaging energy and then developed, resulted in the production of a positive image (i.e. the optical density is greater in the non-exposed areas than in the exposed areas) in contrast to the negative working system which exists in the usual practice of the present invention. The inclusion of reducing sugars in the imaging compositions also enables development of the image, after exposure to imaging energy, to take place at lower temperatures, even at room temperatures, in a period of several hours, for instance, commonly in 10, 12 or 15 hours. The reducing sugars which can be employed are many, illustrative of which are dextrose, glucose, arabinose, erythrose, fructose, galactose, fucose, mannose and ribose. Especially effective are dextrose, arabinose, galactose, fucose and ribose. The reducing sugars can be used in variable amounts, but generally in equivalent amounts, or somewhat smaller or greater, in relation to the amount of imaging materials in the imaging compositions.

In the production of the films or thin layers of the imaging material compositions, which are generally prepared in the form of solutions or homogeneous dispersions and coated or laid down on a substrate, it is especially desirable to dissolve or homogeneously disperse the ingredients in an organic solvent. Illustrative of suitable solvents are chloroform, tetrahydrofuran (THF), dimethylacetamide (DMA), dioxane, dichloromethane and ethylene dichloride, or compatible mixtures of such organic solvents or with other organic solvents. After the solution or homogeneous dispersion is filmed on a substrate in any suitable manner, the major proportions of such organic solvent or solvents are evaporated off, preferably at a relatively low temperature and, sometimes desirably, under subatmospheric pressures or in vacuo, until the film or coating is substantially dry to the touch, such dry to the touch coating being especially desirable for handling and processing purposes. Although such films or coatings may be, generally speaking, dry to the touch, it should be understood that this does not mean that the film is free from organic solvent. Indeed, it has been found that it is frequently very desirable that the finished films or coatings, prior to exposure to imaging energy, contain a small percentage, commonly of the general order of about 2 to 3%, by weight of the film or coating, of organic solvent, for instance, tetrahydrofuran (THF) since its presence appears to play a favorable role in the sensitivity of the system in relation to the latent image formation and/or ultimate image obtained after the development step. The elimination of all or essentially all of the THF, or other organic solvent or solvents, from the virgin film prior to the imaging and development frequently leads to a decrease in sensitivity. In any event, in any given instance where drying of the virgin imaging film has been carried out to a point where essentially no organic solvent is present, and whereby sensitivity is unduly reduced, sensitivity can be increased or restored by adding a small amount of organic solvent to the film prior to exposing it to imaging energy.

The imaging film coating thickness is variable but will usually fall within the range of about 1 to about 25μ with about 5 to 15μ generally being a good average. In thickness in terms of millimeters (mm), such may vary from about 0.0005 to about 0.05mm, or much greater such as from 0.05 to 5mm, the selected thickness being dependent upon the particular use to which the imaging film is to be put.

The production of the imaging materials, and the coating, handling and processing operations, to the extent which may be required, are carried out under appropriate light conditions, as those skilled in the art will readily understand. For instance, the formulation of the coating compositions and the coating and drying operations are conveniently carried out under amberlite filtered light (weak transmission at 550 nm). The dry film prior to imaging is desirably stored in the dark. In certain cases, avoidance of contact of certain of the ingredients with certain metals may be in order where undesired reactions, such as reductions, may occur. In general, the vessels or containers, stirrers, etc. utilized should be made of glass or other vitreous materials or other materials inert to the coating ingredients to insure against contamination or possible undesired reactions. It is advantageous, in general, to prepare the imaging compositions shortly prior to coating them on the selected substrate. Under suitable storage conditions, which generally are conditions of darkness and reasonable avoidance of air or oxidizing atmospheres and humidity conditions, the stability of the imaging compositions is good. Adverse and unduly prolonged storage, however, adversely affects speed and contrast in the production of the images.

In those instances in which the wet process approach is utilized, in which case, as indicated above, it is necessary only to dissolve the tellurium tetrahalide in an organic solvent and contact or impregnate a suitable substrate therewith, and preferably evaporating off, if necessary, only a part of the organic solvent, the solvents utilized should be compatible with the tellurium tetrahalide. The said solvents play a definite role in the intensity of the image obtained. Thus, by way of illustration, solvents such as diethyl ether, tetrahydrofuran (THF) and bis(methoxyl ethyl) ether produce images of strong intensity, whereas images of lesser intensity result from the use of such solvents as tetrahydrofurfuryl alcohol, pinacolone, methyl ethyl ketone, acetone, acetophenone, benzene, ethylene glycol, butyl acetate, methyl isobutyl ketone and anisole. On the other hand, incompatible solvents result in the production of no images or essentially no images and some cause precipitation of the tellurium tetrahalide, illustrative examples of such incompatible solvents being pyridine, aniline, N,N-Dimethyl aniline, phenyl ether, dimethyl formamide, ethylene diamine, tributyl amine, diethyl amine and dimethyl phthalate. The compatibility of any particular solvent can readily be determined by simple test.

It may also be noted that all of the tellurium tetrahalides do not function with equal efficacy and they may function with different efficacies depending upon whether they are used in the wet process procedure or in the making of a dry-to-the-touch film utilizing a matrix and a sensitizer. Thus, for instance, $TeBr_4$ is of no value if used in the wet process procedure but is satisfactory in the dry-to-the-touch film environment.

In the utilization of the films or layers of the present invention, they are subjected, for instance, through a suitable or desired mask, to imaging energy which may, for instance, be by irradiation with ultraviolet light or by visible light, depending, for example, upon the specific imaging material and the specific sensitizer utilized, to form a latent image which is normally not visible to the naked eye. In an illustrative case, for instance, in Example E below, illuminating with a Xenon lamp, the total flux delivered to the film surface may be in the general range of $3 \times 10^5$ to $10^6$ ergs/$cm^2$ of film. The subsequent development, to develop or bring out the latent image, is most desirably effected by the application of heat, for example, at a temperature of about 130°–160° C, preferably about 150° C, for several seconds, say 3 to 15 or 20 seconds, or wet development, or a combination of heat and wet development. Heat or thermal development can be effected by various means such as a hot plate, hot mineral oil, or hot silicone oil, at the aforementioned temperatures, or an infrared lamp. The result is to produce a dark image having, for example, an optical density (O.D.) of 1, in the area of exposure only, the background remaining generally relatively light or clear.

In the development step, only a small percentage of the total imaging material which is present in the matrix composition is reduced to metallic tellurium. After the development, in the case of the production of dry to the touch films using a matrix and a sensitizer, the film or layer is subjected to a fixing step which serves to effect removal of the sensitizer and to inactivate the unreacted imaging compound. While this can be accomplished in various ways, a particularly effective procedure is to wash the film in chloroform-toluene (20:80 by volume) solution saturated with organic amines. This removes the sensitizer and inactivates the imaging material so that no image will form with subsequent exposure and heating and, thus, stabilizes the film. Organic amines such as trimethylamine, triethylamine, diethylamine, triisopropylamine, aniline and benzylamine (e.g. 10% solutions in various solvents such as those noted above) are illustrative of those which can be utilized. Particularly when fixed, the film does not darken, generally speaking, unless subjected to somewhat elevated temperatures as, for instance, of the order of about 90° to 100° C.

The following examples are illustrative of the production of films or layers made in accordance with the present invention. They are not to be construed in any way as limitative of the invention since many other films or layers can be made in light of the guiding principles and teachings contained herein.

EXAMPLE A

FABRICATION OF WET FILM 0.1 g of $TeCl_4$ is dissolved in 3 ml of tetrahydrofuran (THF) to form a slightly yellow clear, homogeneous solution. The solution is deposited onto an inert substrate, e.g., paper, cloth, wood, or the like. Then, while still moist, the film is exposed to ultraviolet light through a mask. In the area of exposure, an image is formed at once without further treatment, said image being composed of tellurium particles. Upon analysis by X-ray, the resulting black image is established as being metallic tellurium, not $TeCl_2$. The intensity of the image varies with the extent of evaporation of the tetrahydrofuran solvent, diminishing in intensity with increasing evaporation of said solvent.

EXAMPLE B 50 mg $TeCl_4$, 250 mg polyvinyl formal ("FORMVAR" 15/95 E), 20 mg o-naphthoquinone and 3 ml THF are stirred together at room temperature until a homogeneous viscous solution is obtained. It is then poured onto a 3 inches × 4 inches sheet of "MYLAR" to form a film or layer of thickness of about 10$\mu$, and then heated in an oven at 50° C for about 30–45 minutes, at which time the film or layer is dry-to-the-touch.

EXAMPLE C

Example B is carried out as described therein except that chloroform is used in place of THF. The film is dried in a well ventilated hood for 30 minutes at room temperature to form a dry-to-the-touch film.

EXAMPLE D

Example B is carried out as described therein except that, in place of the THF, a mixture of THF and chloroform is used in volume ratio of 20% THF – 80% chloroform. A dry-to-the-touch film is obtained.

EXAMPLE E 50 mg $TeCl_2Br_2$, 250 mg polyvinyl formal ("FORMVAR" 15/95 E), 20 mg 9,10-phenanthrenequinone and 3 ml THF are stirred together at room temperature until a homogeneous viscous solution is obtained. It is then poured onto a sheet of "MYLAR" and dried, as described in Example B, to form a clear, dry-to-the-touch film.

EXAMPLE F 50 mg $TeBr_4$, 250 mg polyvinyl formal ("FORMVAR" 15/95 E), 20 mg 9,10-phenanthrenequinone and 3 ml THF are admixed and coated onto "MYLAR" and heated to form a clear dry-to-the-touch film in the manner described in Example B.

EXAMPLE G 50 mg $TeCl_4$, 200 mg cyanoethylated starch, 16 mg 4,5,9,10-pyrenequinone and 2.8 ml THF are stirred together at room temperature until a homogeneous viscous solution is obtained. It is then poured onto a 3 inches × 4 inches sheet of "MYLAR" to form a film or layer of a thickness of about $10\mu$, and then heated in an oven at 50° C for about 30–45 minutes, at which time the film or layer is dry-to-the-tough.

EXAMPLE H 50 mg $TeCl_4$, 250 mg polyvinyl formal ("FORMVAR" 15/95 E), 20 mg, 4,5-pyrenequinone and 3 ml THF are stirred together at room temperature until a homogeneous viscous solution is obtained. It is then poured onto a 3 inches × 4 inches sheet of "MYLAR" to form a clear film or layer of a thickness of about $10\mu$, and then heated in an oven at 50° C for about 30–45 minutes, at which time the film or layer is dry-to-the-touch.

The invention will be further illustrated in connection with the accompanying drawings in which:

FIG. 4 is similar to FIG. 1 but showing the structure fully developed.

FIG. 5 is a schematic representation of a photomicrograph showing in a 2000X enlargement a portion of an area containing a deposit of crystalline image former.

Figure 1:
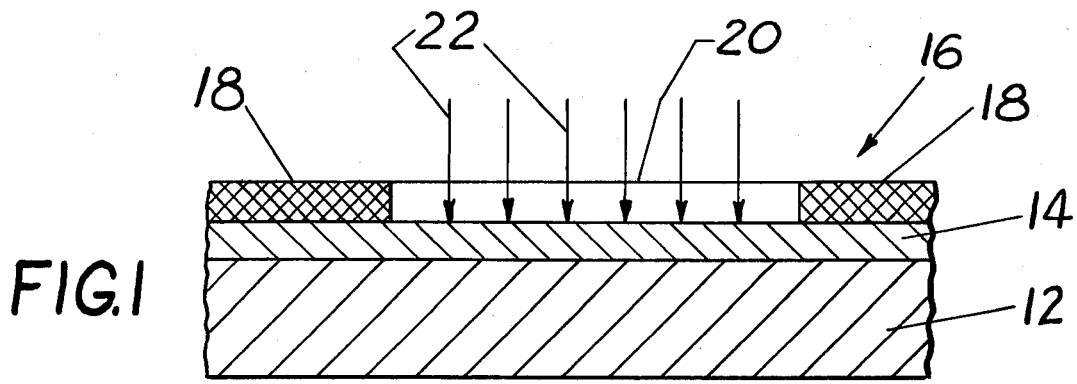
FIG. 1 is a schematical fragmentary cross-sectional representation of a starting structure of the invention comprising a layer containing an imaging material of the type contemplated by the present invention, particularly $TeCl_4$, and being selectively subjected to imaging energy through an opening in a mask.
Figure 2:
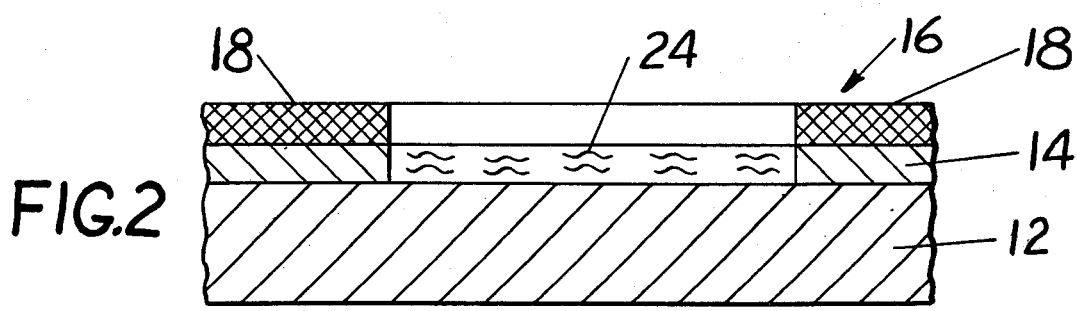
FIG. 2 is similar to FIG. 1, showing the latent image formed by the selective application of imaging energy.

Referring to the drawings, the structure shown in FIG. 1 comprises a substrate 12 such as glass, on which is deposited a thin, light transmissive layer 14 comprising a matrix of a glassy, amorphous material such as polyvinyl formal or cyanoethylated starch and distributed therein $TeCl_4$ as the imaging material and 9,10-Phenanthrenequinone as the sensitizer. Upon the layer 14 of the structure is placed an imaging mask 16 comprising opaque areas 18 and light transmissive area 20. Electromagnetic radiation 22 is shown falling through light transmissive area 20 of the mask. The electromagnetic radiation is being applied in the form of a short pulse. In FIG. 2 is shown the structure of FIG. 1 after termination of the application of electromagnetic radiation. In layer 14 is indicated by small wavy lines the presence of latent image 24, even though this latent image is not necessarily detectable by the eye.

Figure 3:
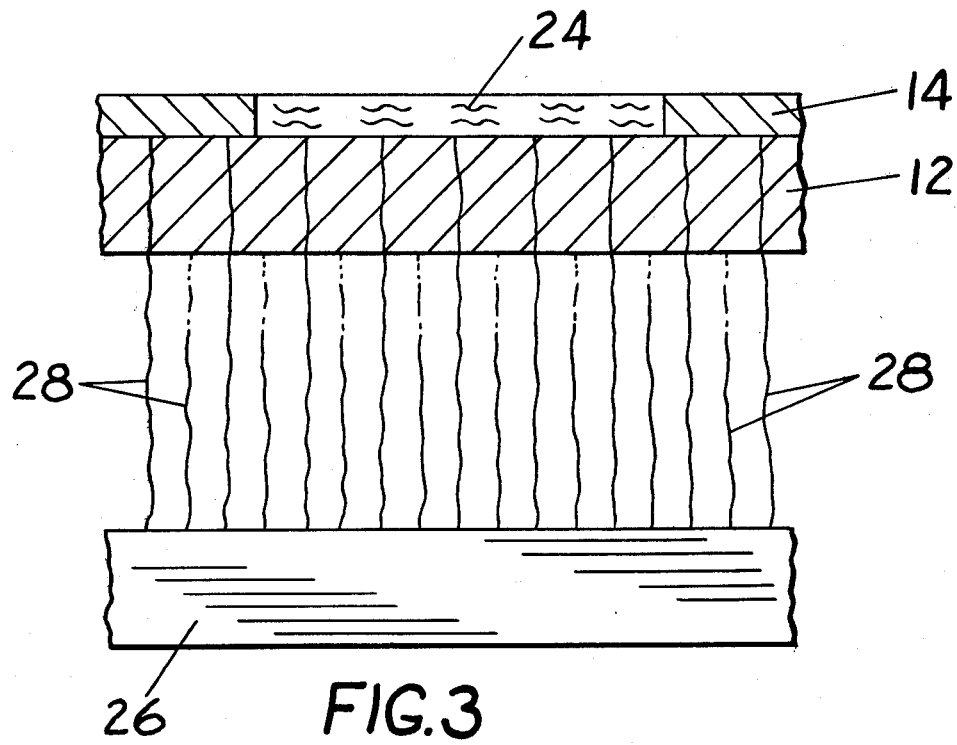
FIG. 3 is similar to FIG. 2 but showing the mask removed and development energy being applied to the structure.

In FIG. 3 is shown the structure of FIG. 2, with latent image 24 in the center section of layer 14. The mask 16 has been removed. The structure is shown suspended above the source 26 of radiant heat, such as an electrical heater, the temperature of which is controlled in the desired range, for instance, 130°–150° C. Radiant heat energy 28 is shown to pass through substrate 12 to heat up the layer 14. As layer 14 is being heated a chemical reaction takes place in the area containing the latent image 24, whereby the tellurium of the above mentioned imaging material is set free from its bonding and precipitated in elementary form in layer 14. The tellurium is present in the area corresponding to the latent image 24 in the layer 14 in form of crystals of very small size. The structure as it appears after completion of the heating step is shown in FIG. 4 comprising an opaque section 30 in the center, where the electromagnetic radiation strikes layer 14, and light transmissive section 32 representing the areas 18 of mask 16 (FIG. 1) from the electromagnetic radiation.

If the subtrate 12 is light transmissive or transparent, such as glass, upon viewing through the structure, area 30 is dark or essentially non-transmissive for light, while areas 32 are highly light transmissive. Such structure therefore represents a transparency.

If the substrate 12 is a non-transparent but highly reflective material such as white paper and layer 14 is originally light transmissive, upon viewing, area 32 will appear white and show the reflectance of the paper, while area 30 is non-reflective appearing dark or black upon reflective viewing.

The separation line at 34 in the structure of FIG. 4 is photographed at an enlargement of 2000X. The appearance of the photomicrograph so obtained is schematically represented in FIG. 5. The separation line of transparent and opaque areas is indicated by the arrow at 34. To the left in the light transmissive area 32 appear no or only a few larger crystals 35 of tellurium while to the right clouds of small particles 35 can be seen. The particles 36 represented in area 30 of FIG. 5 constitute only a few layers upon which the microscope is focused. By visual inspection under the microscope it is seen that there are scattered particles of crystals of tellurium in the layer which produce the opaqueness of area 30.

In the example of the image illustrated in FIG. 5, the tellurium particles representing the image former in area 30, preferably advantageously in the form of needles, have a very narrow size distribution. This is a very favorable characteristic of the imaging materials of the present invention, since it permits the making of high quality images of uniform properties. It permits also to produce a well-balanced gray scale. By varying the composition of the imaging materials, by varying the concentration of the imaging materials in the glassy matrix material and/or by varying the proportion of the sensitizer and by adjusting the imaging and developing conditions, such as the intensity and duration of application of the imaging energy and the intensity and duration of application of the developing energy, the tellurium particle sizes, notably the length of the tellurium needles constituting the image former, may be controlled. Depending on the intended use of the image, one will favor extremely small size needles. In certain cases, increasing the length of the tellurium needles will increase the relative density and contrast, but may reduce the resolution potential of the system. In general, the greater the length of the tellurium needles, leaving everything else equal, the more pronounced will be the photographic gain and the photographic speed of the system. The selection of particular imaging materials which possess variable chemical or other reactivity enables the production of novel photographic systems which, with respect to the resolution, sensitivity to ambient light, photographic sensitivity, speed of development and access to the image, fill various of the needs for which photographic systems are presently used or may be beneficially used.

In another illustrative embodiment of the present invention, utilizing the imaging film of Example B in the structure shown in FIG. 1, an electronic flash gun is used to provide an about 1 millisecond flash of broad spectrum light. The layered structure is then placed for 3 to 15 seconds onto a hotplate, at a temperature of about 130°-140° C, whereby almost instantly a sharp image appears which is an exact negative duplicate of the image represented by the imaging mask. The image has excellent resolution and sharpness.

Although the imaging materials used in the preparation of the iamging film are commonly crystalline in character, the virgin film as laid down in a dry-to-the-touch film on the substrate, and prior to the initial imaging step, appears generally or usually to be non-crystalline so far as has been determined by X-ray diffraction testing. After the development step, the metallic tellurium, advantageously in needle form, appears although particle size and shape due to nucleation and perhaps other forces cause modifications, the exact nature and character of which have not yet been fully delineated. The size of the metallic tellurium needles appears to be affected by such considerations as the imaging film thickness, the character and viscosity of the matrix, the presence and the amount of organic solvent in the film when subjected to imaging energy, and the temperature at which development is effected which also bears upon the color of the final image.

Depending on the desired result in the particular system used, the thickness of the layer 14 (FIG. 1) in the structure of the invention may be varied within wide limits, as heretofore noted. The layer containing the imaging material may be as thin as 1000A or less and as thick as 1mm or more. For producing transparencies or reflection copies, layer thicknesses of about 0.2μm to about 20μm are generally most favorable. The most desirable thickness of the layer depends on such factors as the concentration of the imaging material in the matrix, the nature of the image former, the maximum density desired, the differential in reflection or transmissiveness desired, and on many other factors. In each system one can readily determine the most favorable thickness of the layer by considering these factors. For certain purposes such as recording information in data processing equipment, the layers of the imaging material may be much thicker or thinner than the above stated figures. The formation of nuclei and of the preferred image forming crystallites is influenced to some degree by the thickness of the film. Apparently, surface effects and interfacial effects must be considered in the nucleation reaction and in the reaction leading to the small image forming-crystallites. In selecting the most favorable film thickness of the imaging layer, therefore, also these factors must be considered.

Similar considerations apply to the selection of the concentration of the imaging material in the matrix material. Generally, it is desirable to use the imaging material in as high a concentration as is possible. The functions served by the matrix material have been noted above and require no reiteration. The matrix material itself, and the inclusion of plasticizers, if desired, tend to function as solvents for the imaging materials and to render the film, as desposited and dried, amorphous in character. The compatibility of the matrix materials and the imaging materials appears to add to the sensitivity of a given system and provides better images or better contrast and higher density.

Another relevant consideration is the relationship of the glass transition temperature of the matrix material and the temperature at which cleavage of the molecule of the imaging material used in each instance occurs under the particular reaction condition and in the particular surroundings. If, for instance, the molecule of the imaging material starts to decompose or cleave at a temperature much lower than that of the film, secondary reactions may take place locally which inactivate all or part of the cleavage products of the imaging material which, therefore, lowers the efficiency of the particular imaging system. In certain systems it may be desirable that the cleavage of the imaging material is initiated at a lower temperature than the glass transition temperature of the matrix material, and, when the glass transition temperature is reached in the development step, reaction products migrate to the nucleation sites, delivering the atoms of the metallic tellurium for the building up of the image-forming tellurium needles. Hence, by careful correlation of these factors, better imaging performance can be achieved.

With regard to the substrates, which have been mentioned above and of which certain illustrative examples have been given, it may be observed that the substrate may be any material capable of forming a film or plate, provided that it has a melting or softening point higher than the temperature utilized for the development of the latent image, and provided it is sufficiently unreactive so as not to interfere with the imaging reaction. Suitable substrates are glass, mica, polyamides, polyesters, polystyrenes, hardened condensation polymers such as of the epoxy type, etc. Many heat resistant polymers are commercially available which fulfill these conditions in an excellent manner, and which, therefore, are excellently suited as substrates in the imaging structure of the present invention. For most commercial applications of the imaging materials it is desirable that the substrate be flexible so as to permit use in the form of continuous rolls in printers and in readers. If transparencies are to be produced in a particular imaging system, it is, of course, desirable that the substrate be light transmissive. On the other hand, if copies are to be produced which are to be detected by reflection viewing, it is preferred that a substrate be used which has a high reflectance such as heavily filled white or colored cardboard and other similar structures.

In certain cases, if desired, the substrate may be omitted and layer 14 may be used as a self-supporting structure which is imaged and developed while, for instance, supported on a temporary supporting structure. In this case, the finished image structure consists merely of a thin film of the amorphous glassy matrix material containing incorporated therein the imaging material and sensitizer, plus such additives or supplemental materials as may be used, and the image former precipitated therefrom and transformed therein.

While, as described above, the component ingredients of the imaging composition, namely, the matrix material, the imaging material and the sensitizer, plus such additional or supplemental materials as may be incorporated therewith to obtain particular special properties, are admixed and embodied in a single layer, or as a single layer on a selected substrate, it is within the scope of the invention to utilize a multi-layer system, more particularly a two-layer system. Thus, by way of illustration, one layer can include the sensitizer, for instance, 9,10-phenanthrenequinone carried or distributed in the matrix, for instance, a polyvinyl formal, and supported on a substrate, say a "MYLAR" sheet; and the other layer can include the imaging material carried or distributed in the matrix, which may be the same or a different matrix but, desirably, is the same matrix, and said layer is, likewise, supported on a substrate, say, again a "MYLAR" sheet. Such additional or supplemental materials as may be utilized can be incorporated in whole or in part in either of said layers or distributed through both of said layers. Exposure to imaging energy is then carried out of only the layer containing the sensitizer in which the latent image is formed. The production of the developed or visible image can then be effected, for instance, by pressing the latent image layer against or onto the imaging material-containing layer, in generally sandwich form, and then subjecting the assembly to heat, say at about 150° C for, for instance, of the order of about 15 seconds, the heat being applied from either or both sides through the "MYLAR" substrate or substrates. An image of generally neutral tone promptly appears. This type of procedure provides a favorable alinement simply and with no criticality requirements.

In certain cases, preheating of the virgin imaging film, prior to exposure to imaging energy, at a temperature in the range of 80°-150° C for a few or several seconds, enhances resistance of the virgin imaging film to moisture without adversely affecting the sensitivity of the film.

As noted previously, various forms of energy may be used as the imaging energy and as the development energy. This may include particle energy and wave energy, such as, for instance, electromagnetic radiation, heat, electrons, electrical current, visible light, actinic light or radiation, monochromatic light, laser beams, X-rays, etc. The preferred energy depends also on whether a negative working or a positive working system is employed. In the imaging step, actinic light or electromagnetic radiation is generally used for this step, for instance, light of a wave length of 450nm using a Bausch and Lomb monochromator and a 150 watt Xenon lamp. In the case of the use, for imaging to produce the latent image, of an electron beam, the energy values are variable, generally falling into the range of about 2 Kev to about 100 Kev (a conventional television tube uses an electron beam of about 19 Kev). Thus, by way of illustration using 50 Kev, in which case $E \simeq 3 \times 10^4$ e/cm$^2$, a latent image is obtained which is then developed, for instance, to produce, in any of the manners disclosed herein, a visible image. Radiant electromagnetic radiation is usually best suited to produce an image by projection or by the use of a mask and the like. It is also generally suited best for producing an image having a desired gray scale or tonal gradation. Which kind of electromagnetic radiation or other radiant energy and which wavelength is used in a particular instance depends on the task to be performed and on the particular sensitivity of the imaging material employed. Various of such imaging materials, in the presence of a sensitizer, are sensitive to actinic radiation including laser energy and the like. If a given, selected imaging material is per se insensitive to, or does not have its optimum sensitivity at, a wavelength of actinic light or electromagnetic radiation, which is to be used or available for imaging, selected sensitizers, as noted and indicated above, are added to render the said imaging material sensitive or to shift the sensitivity into the desired range. In this manner, one can, for instance, use an imaging material which has its maximum sensitivity in the range of visible light or for X-rays, etc. Similar considerations apply with respect to the energy used in the development step. Most desirably and advantageously, heat is used for the development. This may be radiant heat such as infrared radiation or microwaves or hot air or heat by contact and convection from a heated body, or it may be heat from a heated wet developing bath. The use of heat for the development offers the advantage that heat may readily be controlled as to intensity and duration. Heat is also inexpensively available from inexpensive equipment. However, if desired, any of the other energy forms may be used for bringing about development of the exposed imaging material, provided it is susceptible to this form of energy.

In each of the imaging and development steps, a combination of different forms of energy may be used. In this case it is preferred to employ a combination of the energy most effective for imaging and of the energy most effective for the development. The development heat may also be supplied by heat generated by the absorption of electromagnetic radiation as is the case with lasers. incandescent lamps, infrared lamps, laser beams, electronic or bulb photoflash units, mercury quartz lamps, etc. can be used for the imaging. In some cases, similar, as well as, of course, other sources can be used for the development.

The energy may be applied for different lengths of time depending on the intensity of the energy source used. With high energy imaging sources, pulses of a microsecond or less to a few milliseconds or more are commonly sufficient to complete the imaging. With lower intensity energy sources, longer times as, for instance, a fraction of a second to several seconds or from 20 to 90 seconds, or more, can be used. Depending on the intended use of the images and on whether or not insensitivity to ambient light is desired, one will select one or the other imaging materials and adapt the imaging time and the intensity and the kind of imaging energy to the requirements of the selected imaging material.

The time of development depends also to a degree on the intensity of the development energy employed, though in this case usually a threshold energy exists which must be exceeded. This threshold is one of intensity —of temperature in the case of heat energy —and must be exceeded to effect development. With the observance of this precaution, development is completed in a second or a few seconds or longer, for instance, of the order of 15 to 20 seconds or, generally, in the range of 5 seconds to 2 minutes, depending on the temperature utilized and on the nature of or the particular imaging material used. The thickness of the layer of said imaging material and the thickness of the substrate may also affect the time required for development. However, in all instances, development is quite rapid so that the said imaging materials and the method of the invention provide reasonably rapid access to the finished stable image. Generally speaking, speed and contrast increase with higher temperatures and longer development times.

Depending on the composition of the imaging material, for instance, it may be desirable to effect the development at a predetermined temperature. As stated, the temperature of development should be adjusted to a level above the threshold, at which the reactions, leading to the formation of the image former, to wit, the precipitation of the metallic tellurium needles, take place. On the other hand, the temperature should not be high enough to cause the thermally induced nucleation and reaction in the areas which have not been subjected to the imaging energy. Usually, the range between these two temperature limits is rather wide, and the temperature can be readily adjusted to fall into the intermediate, useful range. If these precautions are observed, an image of high contrast with low nucleation in the background areas is obtained. In general, where heat development, and particularly dry heat development, is employed, the development temperatures will commonly fall within the range of about 120°-170° C, it being understood that, generally, the lower development temperature the longer will the heating time be required for producing the same optical density. Generally, also, there are, commonly, differences in shades of the final image depending upon the development temperature employed. Again, generally speaking, the effect of appreciably increasing the concentration of the imaging material and the sensitizer is to enable lower development temperatures to be employed where thermal development procedures are utilized. In the thermal development step, depending upon the particular imaging material employed, volatiles are released, such as hydrochloric acid, during the initial stages of decomposition of the imaging materials, which may, and appear to, have an accelerating or autocatalytic effect in the reduction reaction which ultimately results in the formation of tellurium needles and may play a role in such amplification as occurs in the development step.

Wet development can be utilized with or without heat, and where heat is utilized in conjunction with wet development, such heat can be applied extraneously by a heat lamp such as an infrared lamp or the like, or wet developing bath may be applied hot. Such wet development baths may be of various compositions, illustrative thereof being baths consisting of hot inert liquids such as vegetable oils or hydrogenated vegetable oils, silicone oils, glycerin, and the like, or such oils in admixture with minor proportions of the THF and/or a reducing agent such as hydroquinone or reducing sugars such as glucose and dextrose. The inclusion of various additives to the illustrative inert liquids may serve to substantially increase the effective photographic speed of the film, i.e., an appreciably higher optical density can be developed from a smaller exposure. A preferred combination of additives, liquids and bath temperatures is as follows: after exposure to imaging energy as, for instance, to actinic radiation, the film is first submersed for about 5 seconds into a bath consisting of 15 cc of toluene and 15 cc of silicone oil at a bath temperature of about 120° C. Thereafter, the film is placed into a second bath consisting of 20 cc of a vegetable oil (e.g., "Crisco"), 10 cc THF and 90 mg hydroquinone, at a bath temperature of about 140°-150° C. The initial brief period (about 5 seconds) at about 120° C in the first bath serves to form small tellurium nuclei from the photolytically produced tellurium. In the second bath, the THF swells the film, thereby facilitating rapid growth of the nuclei formed in the first bath with the tellurium generated thermally by the heat and chemically by the hydroquinone by reduction of the imaging material. At the same time, the sensitizer, which desirably is 9,10-phenanthrenequinone, is leached out of the film, thereby rendering the image permanently fixed. The development time in the second bath may, for instance, be of the order of 60 to 90 seconds. The bath temperature, the THF concentration and the development times are interchangeable parameters such that a lower bath temperature can be readily accommodated by adjusting the concentration of the THF and the hydroquinone. The increase in photographic speed obtained with the above illustrative development procedure is of the order of 200 fold. This means that, whereas by means of dry development, simply heat as previously described, an optical density of 1.0 is obtained in the film with an exposure of about $10^6$ erg/$cm^2$, the bath development results in an optical density of 1.0 for an exposure of about $6 \times 10^3$ erg/$cm^2$ without adversely affecting the background density.

In any event, after initial exposure to imaging energy, the thus exposed or latent imaged film can be developed immediately or, if desired, even after days or many weeks in storage in the dark or under other non-development storage conditions.

In certain cases, after the formation of the latent image by exposure to imaging energy, the layer or film, prior to development, may be treated with an organic solvent or mixture of organic solvents, for instance, such as THF or mixtures of THF and acetone, to wash out the unreacted sensitizer, while leaving the latent image essentially unaffected. The said layer or film containing the latent image is then subjected to development energy to form the visible image. This procedure, in certain cases, appears to play a favorable role in regard to gain considerations.

The mechanisms of the reactions occurring in the practice of the present invention have not been entirely elucidated, but it appears that exposure of the compositions containing the imaging materials to imaging energy causes the imaging materials to undergo an electronic alteration to an excited state brought aboout by energy transfer from the sensitizer and/or by direct excitation of the imaging material molecule, with the formation of appreciable numbers of nucleation sites or points in the imaged areas and with substantially no or very few such sites or points in the unimaged areas. It appears, further, that absorption of the imaging energy by the sensitizer to form the nucleation sites or points occurs initially on exposure of the imaging material and sensitizer by a hydrogen abstraction mechanism from the polymeric matrix material or the like. The latent image is apparently the result of a chemical modification or photochemical reduction of the sensitizer by the imaging energy in the presence of the imaging material. It appears, although not yet fully ascertained, that the initial latent image of nucleation sites or points which is formed is not defined, produced or delineated by metallic tellurium. It is possible that the initial latent image is made up of several, perhaps four or more compounds, for instance, when 9,10-phenanthrenequinone or analogous compounds are used as the sensitizer. In any event, in the subsequent development step, which provides the needed energy to allow release of tellurium atoms from the imaging material at the nucleation sites or points, which is especially desirably effected thermally or by heat, the imaging material, possibly in a metastable or unstable state, is converted by reaction mechanisms not fully understood but which may involve a reduction reaction by the hydrogen which was abstracted by the sensitizer from the matrix material or by the sensitizer carrying said abstracted hydrogen, whereby to produce a relatively appreciable number of very small metallic tellurium particles, mainly or substantially entirely and advantageously in the form of needles, on the aforementioned nucleation sites or points. Electrons can also act as reducing agents and the materials themselves can also cause reducing.

These metallic tellurium particles, advantageously in the form of needles, act as nuclei upon which further growth of metallic tellurium takes place principally at the ends of said needles to produce longer needles which form and delineate the final developed image. The formation of the metallic tellurium needles by the reduction of the imaging material in the system, and under the conditions existent therein under the initial application of imaging energy followed by development energy, apparently brings about further enhancement of the release of metallic tellurium from the imaging material, which forms a bountiful source of tellurium, to effect, as noted above, further buildup of metallic tellurium on the initially formed metallic tellurium needles and principally at the ends thereof to increase the length thereof. The length-wise growth of the tellurium needles may be enhanced by field concentration at the sharp ends of the needles. The optical density of the final visual image appears to be the result of resonant scattering in addition to light absorption by the tellurium needles. Optical density after development increases initially linearly and then logarithmically with exposure time.

The occurrence of the tellurium particles, which are crystalline in character, is largely or substantially ubiquitous throughout the matrix after development, but only in the illuminated areas are the tellurium crystallites of such dimensions as to optimize the scattering of light which is responsible for the desired visual image. The formation of nuclei which occurs in the background or non-image areas is very substantially less than in the image areas, and they are very widely spaced, and this fact, coupled with the possible somewhat different character of such background nuclei, results in a relatively light background so that good contrast between the image area and the background area is achieved. Furthermore, by careful handling of the imaging materials from the beginning of their production to the imaging, and by effectively excluding carrier-forming energy of damaging intensity prior to exposure to the imaging energy and up to the time of development, the number of metallic tellurium particles in the non-image areas can still be further reduced.

Light or energy absorbed by the sensitizer is effective for the formation of the latent image, and the exposed area becomes depleted in its content of the sensitizer in its original form in the film prior to exposure. Although, as has been indicated above, the latent image which is formed upon exposure to imaging energy is apparently nor formed or delineated by metallic tellurium, it is possible that some metallic or crystalline tellurium, in very small amounts, may be present in the film after exposure to imaging energy and prior to the development step.

Briefly and generally, the imaging layer including the matrix, the imaging material and the sensitizer, as expressed above, is essentially an amorphous structure and it has one detectable characteristic, as for example, it being substantially light transmitting. When the imaging layer is subjected to imaging energy, nucleation sites or points are established in the imaged area of the imaging layer to provide a latent image therein. When the so imaged layer is subjected to development energy, such as heat, the imaging material is reduced and deposits small crystalline metallic tellurium particles at said nucleation sites or points in the latent image, advantageously in the form of small needles, forming small crystalline metallic tellurium nuclei upon which further metallic tellurium is deposited by the further reduction of the imaging material to provide larger crystalline metallic tellurium particles or needles in the imaged area. Thus, the initial structure of the imaging material is changed to a different structure in the imaged area, a crystalline metallic tellurium structure, having another detectable characteristic, for example, it being substantially non-light transmitting. In effect, therefore, the essentially amorphous structure of the imaging layer which is substantially light transmitting is transformed in the imaged area to an essentially crystalline structure which is substantially non-light transmitting to form a visually detectable image. This is accomplished by the various materials, the relations and reactions between the materials and the transformation processes and mechanisms described herein.

In summary, therefore, the mechanisms which come into play in the present invention involve the following considerations:

1. A photosensitive tellurium tetrahalide imaging material which is capable of excitation, under the influence of imaging energy, and in the presence of a sensitizer, to a reactive state and optimumly with good efficiency.
2. The $n\pi^*$ singlet and/or the $n\pi^*$ triplet are the most reactive states, and preferably are the lowest states of the sensitizer.
3. The matrix contains readily easily abstractable or extractable hydrogen atoms.
4. The excited state possesses sufficient energy and a sufficient time period to permit abstracting hydrogen atoms from the matrix by the sensitizer.
5. The imaging material is one which is reactive toward a metastable intermediate to yield Te° needles.

Films made in accordance with this invention may have high photographic resolution, for instance, in various cases, of the order of 500 to 600 line pairs/mm and good continuous tone with gamma close to unity.

The shelf life of the latent image is, generally, good. On unduly prolonged storage, however, of the order of several days or more, development tends to occur at materially lower temperatures than would otherwise be necessary to obtain effective thermal development. Contact of the latent imaged films with various solvents, and dry, wet or low temperature storage generally does not adversely affect the quality of the final image obtained after subsequent thermal development of the latent image.

As to the developed image, its stability is, generally speaking, also good, except, for instance, in the presence of oxidizing agents which cause fading of the image.

The foregoing discussion of the present invention shows that it provides an excellent imaging system which may be widely used for a variety of imaging tasks. The materials of the invention may be employed in the camera, for proofing purposes and for duplication of images, for making duplicate copies of microrecords and microfiche, for recording output information of a computer and for the output of other data storage and retrieval systems. The broad usefulness of the new imaging system of the invention is predicated on the quick and ready access to permanent copy of the information of the record or image. Different methods of readout can be used based upon differences in reflectivity, transparency, opaqueness, electrical properties, the ability to hold electrical charges, etc. The records and images are sharp and have good to excellent resolution. The imaging materials used in the practice of the present invention can be varied from a low gamma to a high gamma as may be needed and desired in each individual instance.

In this respect, the new imaging system, generally speaking, has much of the versitility of the established silver halide system, which by choice of emulsions and development conditions also permits a wide variety of gammas. However, as is readily apparent from the foregoing, the imaging system, as well as the development system, proper, of the present invention does not require wet treatments and, moreover, it provides rapid access to the finished, stable image which is many times not the case with the silver halide images. This makes the new system, particularly in such instances, superior in numbers of respects to the established silver halide systems.

The various other imaging systems which are being used or have recently been proposed as not requiring a wet treatment usually have the disadvantage that they are predicated on the use of a single photosensitive material with little possibility of varying the character of the material such as varying the gamma of the image. They may, therefore, be suitable in one particular application but are not suitable in any other applications. The imaging materials used in the imaging system of the present invention are, generally speaking, inexpensive and may readily be applied by inexpensive methods so that a low cost imaging system is provided.

The present invention does not require vacuum deposition or sputtering of an elementary image former onto a substrate. The imaging compositions may readily be applied in form of a solution e.g. by wiping, spin deposition, application by a doctor knife, etc. The images produced by the practice of the present invention can be used as a print master, e.g. when an image former is selected which has a capacity for accepting and holding electrical charges differently from the matrix material. In this case, the images can be produced, for instance, on a paper or cardboard substrate to provide an inexpensive throwaway printing master. After a desired number of copies have been made from it, the print master is simply discarded.

We claim:

1. A method for producing a record of retrievable information:
    providing a layer which comprises an imaging material in the form of a tetrahalide of tellurium in which the halide is at least one member selected from the group consisting of chlorine and bromine, said imaging material having one detectable characteristic and which is capable of undergoing a chemical change in response to the application of energy to produce a material of different chemical character having another detectable characteristic, said imaging material being dissolved or dispersed in a polymeric matrix material,
    the step of applying imaging particle or wave radiation to at least a certain portion of said layer to bring the chemical change in said imaging material in said certain portion of said layer to produce said material of different chemical character and to record the desired information in said layer.

2. The method of claim 1, in which said imaging radiation comprises electromagnetic radiation.

3. The method of claim 1, in which said layer comprises also a spectral sensitizer to modify the sensitivity of said imaging material to a given imaging radiation.

4. The method of claim 3, in which said imaging material and the sensitizer are dissolved in said polymeric matrix material, said polymeric matrix material being at least in part of amorphous character.

5. The method of claim 4, in which said imaging material is $TeCl_4$.

6. A method for producing an image comprising:
    providing a layer which comprises an imaging material having the formula $TeCl_nBr_m$ where $n$ is an integer from 2 to 4 and m is an integer from 0 to 2 with the proviso that the sum of n and m equals 4, said imaging material being dissolved or dispersed in a polymeric matrix material,
    applying imaging particle or wave radiation to at least a certain portion of said layer to decompose said imaging material to form a latent image,
    and then subjecting said latent image to heat or reducing sugars to convert said latent image into a developed image which is defined by crystals of tellurium.

7. The method of claim 6, in which said imaging material comprises $TeCl_4$.

8. The method of claim 7, in which said layer comprises also a spectral sensitizer to modify the sensitivity of said imaging material to a given imaging radiation.

9. The method of claim 8 in which said imaging material and the sensitizer are dissolved or dispersed in said polymeric matrix material, said polymeric matrix material being at least in part of amorphous character.

10. The method of claim 9, in which the imaging material is sensitive to visible light.

11. The method of claim 9, in which the imaging material is sensitive to ultraviolet light.

12. The method of claim 9, in which the imaging radiation is electromagnetic radiation and in which the development energy is heat.

13. A method for producing a record of retrievable information comprising:
    providing a layer in the form of a matrix of a glassy, amorphous material which has a glass transition temperature and which carries an imaging material in the form of a tetrahalide of tellurium in which the halide is at least one member selected from the group consisting of chlorine and bromine, said imaging material being of one structure and having one detectable characteristic which is capable of undergoing a change in response to the application of imaging radiation to produce a material of different structure having another detectable characteristic, selectively subjecting said layer to imaging particle or wave radiation to form a latent image, with or without the aid of a spectral sensitizer, which latent image is essentially not a record of retrievable information; and developing, through the utilization of heat, either simultaneously with or subsequently to the application of the imaging radiation, to produce in the exposed areas an image which is a record of retrievable information constituted by atoms of the element tellurium.

14. The method of claim 13, in which said radiation applied to said layer is electromagnetic radiation.

15. The method of claim 14, in which the glassy amorphous material is polyvinyl formal.

16. The method of claim 15, in which the imaging material comprises $TeCl_4$.

17. A method for producing a record of retrievable information comprising:

the step of applying a solution of an imaging material to a substrate to lay down a layer of said imaging material on said substrate, said imaging material having the formula $TeCl_nBr_m$ where n is an integer from 2 to 4 and m is an integer from 0 to 2 with the proviso that the sum of n and m equals 4, said imaging material being dissolved or dispersed in a polymeric matrix material, then, while said layer is still moist from said solution, applying imaging electromagnetic radiation to at least a certain portion of said layer to bring about a chemical change in said imaging material in said certain portion of said layer to produce a material of different chemical character and to record the desired information in said layer.

18. The method of claim 17, in which the imaging material is a member selected from the group consisting of $TeCl_4$ and $TeCl_2Br_2$.

19. The method of claim 18, in which the electromagnetic radiation is ultraviolet light.

20. In a method for producing a record of retrievable information, the steps which include providing, on a substrate, a matrix containing an imaging material and a spectral sensitizer, said matrix comprising polymeric material which is at least in part amorphous, and said imaging material comprising $TeCl_4$, applying imaging particle or wave radiation to a portion of said layer to bring about decomposition of said imaging material to produce metallic tellurium and a latent image in those areas where said imaging radiation is applied.

21. The method of claim 20, in which heat is applied to said latent image to effect development thereof.

22. The method of claim 21, in which the sensitizer is phenanthrenequinone.

23. The method of claim 1, in which said imaging radiation is applied simultaneously with development energy in the form of heat.

24. The method of claim 1, in which the imaging radiation is radiant radiation, and in which heat is applied to effect development subsequent to the application of the imaging radiant radiation.

25. The method of claim 1, in which the imaging layer containing the imaging material is in amorphous form and in which said imaging material is transformed by the radiation into a metallic tellurium having a crystalline structure.

26. An article for producing a record of retrievable information comprising a layer of an imaging material and a spectral sensitizer on a substrate, said imaging material comprising a tetrahalide of tellurium in which the halide is at least one member selected from the group consisting of chlorine and bromine, said imaging material having one detectable characteristic and which is capable of undergoing a chemical change in response to the application of particle or wave radiation to produce a material of different chemical character having another detectable characteristic, said imaging material and spectral sensitizer being dissolved or dispersed in a polymeric matrix material.

27. The article of claim 26, in which the imaging material comprises $TeCl_4$.

28. An article for producing a record of retrievable information in the form of a dry to the touch film or layer comprising a matrix containing an imaging material and a spectral sensitizer, said matrix comprising polymeric material which is at least in part amorphous, and said imaging material comprising a tetrahalide of tellurium in which the halide is at least one member selected from the group consisting of chlorine and bromine, said imaging material having one detectable characteristic and which is capable of undergoing a chemical change in response to the application of particle or wave radiation to produce a material of different chemical character having another detectable characteristic.

29. The article of claim 28, in which the imaging material comprises $TeCl_4$.

30. The article of claim 29, in which the sensitizer is phenanthrenequinone.

* * * * *